(12) United States Patent
Thorpe et al.

(10) Patent No.: US 9,726,682 B2
(45) Date of Patent: Aug. 8, 2017

(54) APPARATUS FOR ADMINISTERING FLUID TO A MEDICAL TUBE

(71) Applicant: CME UK (HOLDINGS) LIMITED, Blackpool Lancashire (GB)

(72) Inventors: Stephen Thorpe, Poulton-le-Fylde (GB); Anat Barak, Caesarea (IL)

(73) Assignee: CME UK (HOLDINGS) LIMITED, Blackpool Lancashire (GB)

( * ) Notice: Subject to any disclaimer, the term of this patent is extended or adjusted under 35 U.S.C. 154(b) by 14 days.

(21) Appl. No.: 14/377,060

(22) PCT Filed: Feb. 5, 2013

(86) PCT No.: PCT/GB2013/050260
§ 371 (c)(1),
(2) Date: Aug. 6, 2014

(87) PCT Pub. No.: WO2013/117916
PCT Pub. Date: Aug. 15, 2013

(65) Prior Publication Data
US 2014/0378894 A1  Dec. 25, 2014

(30) Foreign Application Priority Data
Feb. 6, 2012  (GB) .................................. 1202002.0

(51) Int. Cl.
| | |
|---|---|
| *G01N 33/00* | (2006.01) |
| *G01N 33/84* | (2006.01) |
| *G01N 33/487* | (2006.01) |
| *A61J 15/00* | (2006.01) |
| *A61M 1/00* | (2006.01) |
| *A61M 39/10* | (2006.01) |
| *A61M 39/00* | (2006.01) |
| *A61B 90/00* | (2016.01) |

(52) U.S. Cl.
CPC .......... *G01N 33/84* (2013.01); *A61J 15/0003* (2013.01); *A61J 15/0026* (2013.01);
(Continued)

(58) Field of Classification Search
CPC .. A61J 15/0026; A61J 15/008; A61J 15/0084; G01N 1/10; G01N 33/48;
(Continued)

(56) References Cited

U.S. PATENT DOCUMENTS

| | | |
|---|---|---|
| 3,373,735 A | 3/1968 | Gallagher |
| 4,381,011 A | 4/1983 | Somers |

(Continued)

FOREIGN PATENT DOCUMENTS

| | | | |
|---|---|---|---|
| EP | 1774985 A1 | 4/2007 | |
| EP | 2168558 A1 | 3/2010 | |
| EP | 2481351 | * 8/2012 | ............. A61B 5/061 |

OTHER PUBLICATIONS

International Search Report for application No. PCT/GB2013/050260, dated May 7, 2013, 6 pages.
(Continued)

*Primary Examiner* — Benjamin Schmitt
(74) *Attorney, Agent, or Firm* — Reising Ethington P.C.

(57) ABSTRACT

An apparatus for use in tube feeding has a cylindrical body provided with first opening and second openings connected by a flow channel. The body has a reagent, for determining a characteristic of fluid disposed in the body and a transparent window to view the reagent. In use, a first end of an internal feeding tube releasably engages with the first opening. The second, distal end of the feeding tube is disposed inside a patient. A second feeding tube engages with the second opening. The second feeding tube connects the apparatus to a bi-directional pump operable: to pump internal fluid from a reservoir, through the apparatus and into the internal feeding tube; and to pump fluid from the patient into the body of the apparatus. This allows a user to pump fluid from the patient into the body of the apparatus to react with the reagent.

9 Claims, 2 Drawing Sheets

(52) U.S. Cl.
CPC ....... *A61J 15/0084* (2015.05); *A61J 15/0092* (2013.01); *A61M 1/008* (2013.01); *A61M 39/10* (2013.01); *G01N 33/487* (2013.01); A61B 2090/0807 (2016.02); A61J 15/0076 (2015.05); A61J 2015/0088 (2013.01); A61M 2039/0009 (2013.01); A61M 2039/1038 (2013.01); A61M 2205/18 (2013.01); A61M 2205/583 (2013.01)

(58) Field of Classification Search
CPC ...... G01N 33/487; G01N 33/50; G01N 33/52; G01N 33/84
USPC .................. 604/30, 65, 257; 73/53.01, 61.41
See application file for complete search history.

(56) References Cited

U.S. PATENT DOCUMENTS

| | | |
|---|---|---|
| 5,085,216 A | 2/1992 | Henley, Jr. |
| 5,197,464 A | 3/1993 | Babb |
| 5,800,779 A | 9/1998 | Johnson |
| 2008/0004598 A1 | 1/2008 | Gilbert |
| 2009/0198182 A1* | 8/2009 | Fujishima ............... A61L 29/14 604/131 |
| 2010/0030133 A1* | 2/2010 | Elia ........................ A61B 5/037 604/28 |
| 2010/0081896 A1* | 4/2010 | Swisher ............. A61B 17/3415 600/309 |
| 2011/0046653 A1 | 2/2011 | Addington |
| 2011/0270054 A1 | 11/2011 | Carr |
| 2012/0208285 A1* | 8/2012 | Deighan ................ A61B 5/061 436/163 |

OTHER PUBLICATIONS

Written Opinion of the International Searching Authority for application No. PCT/GB2013/050260, dated May 7, 2013, 6 pages.
Search Report under Section 17 for Application No. GB1302033.4 dated Jun. 5, 2013, 2 pages.
Examination Report under Section 18(3) for Application No. GB1302033.4 dated Jan. 19, 2017, 4 pages.

* cited by examiner

APPARATUS FOR ADMINISTERING FLUID TO A MEDICAL TUBE

TECHNICAL FIELD

The present invention relates to an apparatus for attachment to medical tube used to administer fluid. In particular, it relates to an apparatus that is suitable for attachment to an internal feeding tube.

BACKGROUND

There are several situations wherein a patient suffers from a condition that renders it difficult, unsafe or impossible, either temporarily or permanently, to take food through their mouth. In such situations it is known to use a tube to feed the patient. This process is referred to as gavage, internal feeding or tube feeding. Essentially, tube is placed so that one end thereof is disposed in the stomach of the patient and fluids containing food and/or medicine are pumped into the stomach from the other end of the tube. A variety of feeding tubes are used in medical practice, as required by the condition of the patient.

The placement of the tube may be temporary or life-long depending on the condition of the patient and a number of alternative methods can be employed. For relatively short term one end of a nasogastric feeding tube may be inserted through the nasal cavity and fed down the oesophagus and into the stomach. Patients requiring longer term therapy may be provided with a more permanent solution such as a percutaneous endoscopic gastrostomy (PEG) which is passed into the stomach of the patient through their abdominal wall.

It is widely accepted as essential practice that medical staff should confirm that one end thereof is disposed in the stomach before fluids are administered via the tube. This is essential because between feeds movement of the patient can result in migration of the end of the feeding tube. For example, the end of the feeding tube may migrate to the oesophagus of lungs. Administration of fluids into the lungs could result in serious harm to the patient and could even be fatal.

There are three known methods for verifying the position of the end of the feeding tube that are practiced to date.

The first method involves connecting a syringe to a first end of the feeding tube and drawing up a sample of fluid therefrom. The syringe is removed from the feeding tube and the acidity of fluid is tested using pH indicator strips or paper. If the acidity of the fluid matches that of gastric juices then it is assumed that the other, second end of the feeding tube is disposed in the stomach and the medical staff can safely administer fluid via the feeding tube. This method requires at least two connections to be made to the feeding tube per feed, each connection carrying a risk of contaminating the feeding tube. It requires several steps to be followed by the medical staff, can be time consuming and could lead to the medical staff sustaining a repetitive strain injury. Furthermore, whilst using this method there is a risk that medical staff may be exposed to bodily fluids of the patient.

A second method relies upon the use of an X-ray to confirm the position of an end of the feeding tube. This method is rather expensive and relies upon bulky inconvenient apparatus. Furthermore, this method poses additional health risks, such as an increased risk of developing cancers, to the patient and medical staff, especially if used frequently and/or over a prolonged period of time.

A third known method is known as auscultation. This involves connecting a syringe to a first end of the feeding tube, injecting air into the feeding tube and listening, using a stethoscope, for the sound of bubbling at the other, second end. If bubbling is identified then it is assumed that the other, second end of the feeding tube is disposed in the stomach and the medical staff can safely administer fluid via the feeding tube. This involves a significant degree of skill and it therefore unsuitable for use by inexperienced or untrained medical staff. There is also greater scope for human error to result in a misidentification of the position of the second end of the feeding tube than with the other two methods.

It is an object of embodiments of the present invention to at least partially overcome or alleviate the above problems.

SUMMARY

According to a first aspect of the present invention there is provided an apparatus suitable for use in a tube feeding system said apparatus comprising a body provided with a first opening and a second opening, wherein: a first engagement means is provided to allow releasable engagement of the apparatus with a first fluid carrying element so that the first opening is aligned with said first fluid carrying element; a second engagement means is provided to allow releasable engagement of the apparatus with a second fluid carrying element so that the second opening is aligned with said second fluid carrying element; and the first and second openings are connected so as to allow fluid to flow therebetween in either direction, characterised in that the body comprises a means for determining a characteristic of fluid disposed therein.

Such an apparatus allows a characteristic of a fluid that is pumped either way through a fluid carrying system to be determined.

The first fluid carrying element may comprise a tube. The tube may comprise an internal feeding tube. Said feeding tube may be any type of feeding tube and in particular may be a nasogastric feeding tube or a percutaneous endoscopic gastrostomy (PEG).

The second fluid carrying element may comprise, or be connected to, a means for drawing fluid out of the first fluid element and into the apparatus. The means for drawing fluid out of the first fluid element and into the apparatus may comprise a pump. The second fluid carrying element may comprise, or be connected to, a means for introducing fluid into the apparatus from the second fluid element. The means for introducing fluid into the apparatus from the second fluid element may comprise a pump. The means for drawing fluid out of the first fluid element and into the apparatus and the means for introducing fluid into the apparatus from the second fluid element may be combined and may comprise a bi-directional infusion pump.

The characteristic of fluid drawn out of the tube may comprise its acidity. The means for determining a characteristic of fluid disposed in the body may comprise a reagent. The reagent may comprise a pH indicator.

Therefore, the apparatus according to the first aspect of the present invention can be connected in line between a feeding tube and a pump operable to pump internal fluid therethrough. Advantageously, this allows a user to ensure correct placement of internal feeding tubes prior to administering internal fluids. The principle is similar to a prior art technique but use of the apparatus according to the present invention reduces the number of connections and/or disconnections that need to be made to a feeding tube in order to aspirate a quantity of fluid therefrom and to introduce a quantity of fluid therein. Advantageously, this reduces the risk of contaminating the tube. This in turn can reduce the risk of infecting a patient that is being fed using the apparatus according to the present invention. The apparatus according to the present invention therefore simplifies the process; it can ensure that all necessary steps to check the location of a feeding tube are performed prior to feeding; it reduces the number of physical operations required of the user; and it reduces the risk that a user will come into contact with bodily fluids of a patient. The apparatus according to the present invention also reduces the amount of medical waste that must be disposed of relative to prior art techniques.

For embodiments comprising means for drawing fluid out of the first fluid element and into the apparatus, preferably, the second fluid carrying element is provided with a non-return valve. Advantageously, this can prevent fluids drawn out of the first fluid element from entering the second fluid element. This is particularly advantageous if the apparatus is used in a tube feeding system as it can allow a pump to aspirate fluid out of a feeding tube and into the apparatus so that a characteristic of the fluid may be determined whilst preventing the aspirated fluid from entering the pump.

The first and second engagement means may be of any suitable form as desired or required. The first and/or second engagement means may be arranged so as to allow a push fit or screw fit engagement between the apparatus and the tube.

The second fluid carrying element may comprise, or be connected to, a reservoir containing fluid that it is desired to be introduced into the first fluid carrying element.

The apparatus may comprise a comparison means. The comparison means may be operable to compare the characteristic of the fluid drawn out of the tube as determined by the apparatus with predetermined criteria. For example, for embodiments wherein the characteristic is the acidity of the fluid, the criteria may require that the pH value of the fluid lies in a certain range. This range may coincide with the typical range of pH values of gastric juices. The comparison means may be operable to output a signal indicating whether or not the predetermined criteria are met. Said signal may be a digital signal. In the event that the predetermined criteria are not met the means for introducing fluid into the first end of the tube may be disabled or locked so as to prevent fluid from being introduced into the tube.

The apparatus may comprise an indicator means. The indicator means may be operable to display a visual indication of the characteristic of the fluid drawn out of the tube. Additionally or alternatively, the indicator means may be operable to display a visual indication of the signal output by the comparison means. The indicator means may be implemented as a substantially transparent window in the body which allows a user to visually inspect means for determining a characteristic of fluid. For example, the body may comprise a transparent section allowing a user to view a pH indicator located within the body.

The apparatus may comprise a means for adjusting the flow of fluid through the body. This may comprise a valve. This can allow the speed and pressure to be varied for different fluid carrying systems.

Preferably, the apparatus is provided as a single closed system. The single closed system may be produced in sterile conditions and packaged so as to remain sterile until a user opens the packaging. Such an arrangement need only be removed from its sterile packaging and engaged with a first fluid carrying element and a second fluid carrying element. Advantageously, this minimises the number of operations that must be performed by the user in a non-sterile atmosphere which in turn reduces the risk of contaminating the first fluid carrying element.

According to a second aspect of the present invention there is provided an apparatus for attachment to a tube comprising: an engagement means arranged to allow releasable engagement of the apparatus with a first end of a tube; a means for drawing fluid out of the first end of the tube; a means for determining a characteristic of fluid drawn out of said tube; and a means for introducing fluid into the first end of the tube.

Such an apparatus advantageously allows a user to confirm that one end of a tube is disposed in a desired location and to subsequently administer fluid to said desired location whilst only requiring a single connection to be made. This reduces the number of connections and/or disconnections that need to be made to a tube in order to aspirate a quantity of fluid therefrom and to introduce a quantity of fluid therein. Advantageously, this reduces the risk of contaminating the tube.

The tube may comprise an internal feeding tube. Said feeding tube may be any type of feeding tube and in particular may be a nasogastric feeding tube or a percutaneous endoscopic gastrostomy (PEG).

For such embodiments, the apparatus according to the present invention allows for user to ensure correct placement of internal feeding tubes. It simplifies the process; it can ensure that all necessary steps are performed; it reduces the number of physical operations required of the user; and it reduces the risk that a user will come into contact with bodily fluids of a patient.

The apparatus according to the present invention reduces the amount of medical waste that must be disposed of relative to prior art techniques.

The apparatus may comprise a modular system. Preferably, the means for determining a characteristic of fluid drawn out of the tube is provided as a separate, closed system that can be detached from other elements of the apparatus. Advantageously, this can allow the means for determining a characteristic of fluid drawn out of the tube to be provided as a one use, disposable element whilst the other elements may be used repeatedly. This is particularly advantageous if the apparatus fours part of a tube feeding system since it is undesirable to use an element used to aspirate fluids from a patient more than once whereas it is desireable to re-use other elements of the system, such as the pump.

The separate, closed system may be produced in sterile conditions and packaged so as to remain sterile until a user opens the packaging. Such an arrangement need only be removed from its sterile packaging and engaged with a tube. Advantageously, this minimises the number of operations that must be performed by the user in a non-sterile atmosphere which in turn reduces the risk of contaminating the tube.

The apparatus according to the second aspect of the present invention may comprise an apparatus according to the first aspect of the present invention. In particular, the means for determining a characteristic of fluid drawn out of the tube may be provided by an apparatus according to the first aspect of the present invention. For such embodiments, the apparatus according to the second aspect of the present invention may comprise any or all of the features of the first aspect of the present invention as desired or required.

Preferably, the means for determining a characteristic of fluid is disposed between the first end of the tube and the means for drawing fluid out of the first end of the tube.

The apparatus may be provided with a non-return valve. The non-return valve may be disposed between the means for detenning a characteristic of fluid and the means for drawing fluid out of the first end of the tube. Advantageously, this can prevent fluids drawn out of the first end of the tube from coming into contact with the means for drawing fluid out of the first end of the tube. This is particularly advantageous if the apparatus is used in a tube feeding system as it can allow a pump to aspirate fluid out of a feeding tube and into a body so that a characteristic of the fluid may be determined whilst preventing the aspirated fluid from entering the pump.

The engagement means may be of any suitable form as desired or required. The engagement means may be arranged so as to allow a push fit or screw fit engagement between the apparatus and the tube.

The means for drawing fluid out of the first end of the tube may comprise a pump. The means for introducing fluid into the first end of the tube may comprise a pump. The means for drawing fluid out of the first end of the tube and the means for introducing fluid into the first end of the tube may be combined and may comprise a bi-directional infusion pump.

The apparatus may comprise a reservoir containing fluid that it is desired to be introduced into the first end of the tube. Alternatively, the apparatus may comprise a second engagement means arranged to allow releasable engagement of the apparatus with a reservoir containing fluid that it is desired to be introduced into the first end of the tube. The apparatus may be attached directly to a reservoir or via an intermediate component such as a second tube. The second engagement means may be of any suitable form as desired or required and may be arranged so as to allow a push fit or screw fit engagement between the apparatus and the reservoir.

The characteristic of fluid drawn out of the tube may comprise its acidity. The means for determining a characteristic of fluid disposed in the body may comprise a reagent. The reagent may comprise a pH indicator.

The apparatus may comprise a comparison means. The comparison means may be operable to compare the characteristic of the fluid drawn out of the tube as determined by the apparatus with predetermined criteria. For example, for embodiments wherein the characteristic is the acidity of the fluid, the criteria may require that the pH value of the fluid lies in a certain range. This range may coincide with the typical range of pH values of gastric juices. The comparison means may be operable to output a signal indicating whether or not the predetermined criteria are met. Said signal may be a digital signal.

The apparatus may comprise an indicator means. The indicator means may be operable to display a visual indication of the characteristic of the fluid drawn out of the tube. Additionally or alternatively, the indicator means may be operable to display a visual indication of the signal output by the comparison means. In the event that the predetermined criteria are not met the means for introducing fluid into the first end of the tube may be disabled or locked so as to prevent fluid from being introduced into the tube.

The apparatus may comprise an actuation means. The actuation means may be operable to cause the apparatus to draw a quantity of fluid out of the first end of the tube and to determine the characteristic of said fluid. The actuation means may further be operable to cause the apparatus to introduce fluid into the first end of the tube.

The apparatus may comprise a processing means. The processing means may be operable to control: the means for drawing fluid out of the first end of the tube; the means for determining a characteristic of fluid drawn out of said tube; the means for introducing fluid into the first end of the tube; and the comparison means. The processing means may be programmable. The processing means may be programmed so as to ensure that local guidelines or regulations are followed.

In a preferred embodiment, once the apparatus has been releasably engaged with a first end of a tube the actuation means may be operable to cause the apparatus to: draw a quantity of fluid out of the first end of the tube; determine the characteristic of said fluid; and compare the determined characteristic with predetermined criteria. These functions are preferably controlled by the processing means. The quantity of fluid drawn into the apparatus may be a fixed or pre-set quantity. For example, the quantity may be chosen to be of the order of, or slightly greater than, the volume of the feeding tube. This ensures that at least some of said fluid has been drawn into the feeding tube from the locality of the first end of the feeding tube. If the predetermined criteria are met then the processing means may automatically cause fluid to be pumped into the first end of the tube from a reservoir. Alternatively, the indication means may provide a visual indication that the criteria are met. This may prompt a user to use the actuation means to cause fluid to be pumped into the first end of the tube from a reservoir.

Preferably, the speed and pressure at which fluid is drawn out of and introduced into the first end of the tube can be controlled. This can allow the speed and pressure to be varied for different tubes so as to optimise the time taken for a fixed quantity of fluid to be drawn out of or introduced into the tube.

The apparatus may be provided with a control unit. The control unit may comprise the actuation means and/or the indicator means. The control unit may be connected to the processing means. Therefore the control unit can provide a user interface for the processing means. In a particularly preferred embodiment, the control unit comprises a housing wherein a surface of the housing is provided with an input means and a display means. The input means may comprise one or more buttons, a touchpad or any other means for inputting control commands. The display means may comprise a transparent section of the housing, an LCD display, an LED display or any other visual indication as desired or required. The input means and the display means may be integrated. Such an integrated input and display means may comprise a touchscreen or similar hardware.

According to a third aspect of the present invention there is provided a control unit for an apparatus according to the second aspect of the present invention comprising: a housing wherein a surface of the housing is provided with a input means and a display means.

The input means according to the first aspect of the present invention may comprise any or all of the features of the apparatus according to the second aspect of the present invention as desired or required.

The control unit may comprise the actuation means and/or the indicator means.

The control unit may be connected to the processing means. Therefore the control unit can provide a user interface for the processing means.

The input means may comprise one or more buttons, a touchpad or any other means for inputting control commands.

The display means may comprise a transparent section of the housing, an LCD display, an LED display or any other visual indication as desired or required.

The input means and the display means may be integrated. Such an integrated input and display means may comprise a touchscreen or similar hardware.

In a preferred embodiment, the control unit is operable to cause the apparatus to aspirate a quantity of fluid out of the tube. Preferably, the display means subsequently displays a prompt to a user indicating whether or not it is safe to introduce fluid into the tube. The input means may then be operable to cause a quantity of fluid to be introduced into the tube.

According to a fourth aspect of the present invention there is provided a method of determining the location of a first end of a feeding tube using an apparatus according to the first aspect of the present invention comprising the steps of: releasably engaging the apparatus according to the first aspect of the present invention with a second end of the feeding tube using the first engagement means; releasably engaging the apparatus according to the first aspect of the present invention with a means for drawing fluid out of the feeding tube and into the apparatus using the second engagement means; using said means to draw a quantity of fluid out of the feeding tube and into the apparatus; and determining a characteristic of said fluid.

The method according to the fourth aspect of the present invention may incorporate any or all of the features of the apparatus according to the first, second or third aspects of the present invention as desired or required.

The quantity of fluid drawn into the apparatus may be a fixed or pre-set quantity. For example, the quantity may be chosen to be slightly greater than the volume of the feeding tube. This ensures that at least some of said fluid has been drawn into the feeding tube from the locality of the first end of the feeding tube.

The characteristic of fluid drawn out of the tube may comprise its acidity. The means for determining a characteristic of fluid disposed in the body may comprise a reagent. The reagent may comprise a pH indicator.

The apparatus may additionally be provided with a means for introducing fluid into the apparatus and the method may further comprise the step of introducing fluid into the apparatus. This step may be dependent upon the characteristic of the fluid as previously determined. For example, this step may only be performed if the acidity of the fluid drawn out of the feeding tube coincides with that of gastric juices.

The method may form part of a method of tube feeding a patient using an internal feeding tube.

BRIEF DESCRIPTION OF THE DRAWINGS

In order that the invention may be more clearly understood embodiments thereof will now be described, by way of example only, with reference to the accompanying drawings, of which.

DETAILED DESCRIPTION OF THE ILLUSTRATED EMBODIMENT(S)

Figure 1:
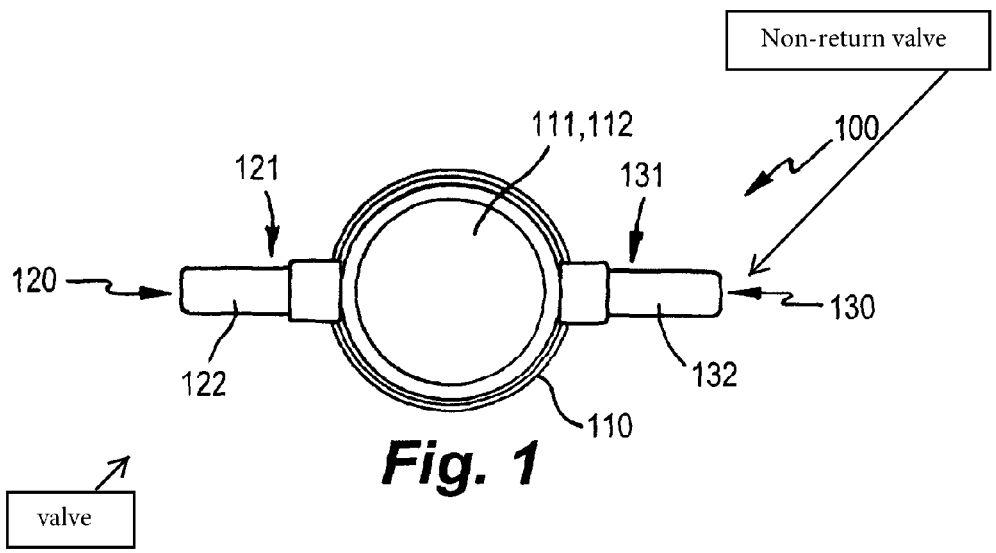
FIG. 1 is a plan view of an apparatus according to the first aspect of the present invention.
Figure 2:
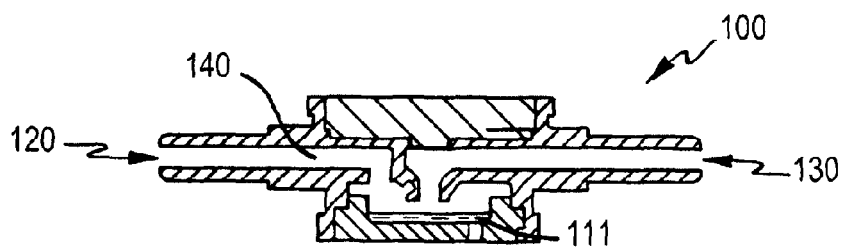
FIG. 2 is a cross sectional view of an apparatus according to the first aspect of the present invention.
Figure 3:
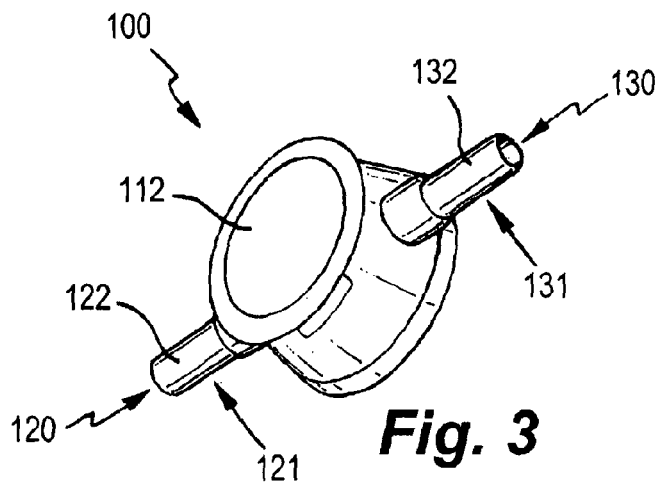
FIG. 3 is a perspective view of an apparatus according to the first aspect of the present invention.

Referring to FIGS. 1-3, an apparatus 100 suitable for use in the fluid carrying system used for tube feeding according to the first aspect of the present invention comprises a generally cylindrical body 110 provided with a first opening 120 and a second opening 130. The first opening 120 is provided at the end of a first generally cylindrical protrusion 121 and the second opening 130 is provided at the end of a second generally cylindrical protrusion 131. The first and second protrusions 121,131 are provided on a curved surface of the body 110 and are diametrically opposed.

The first and second protrusions 121,131 are each provided with reduced diameter section 122,132 in the region proximate to the first and second openings 120,130 respectively. These reduced diameter sections 122,132 constitute a male member that can facilitate releasable engagement with a tube (not shown) and thereby constitute first and second engagement means respectively.

The apparatus 100 may be formed from any suitable material and is preferably formed from a plastics material.

As can be seen in FIG. 2, the first and second openings are connected by a flow channel 140 so as to allow fluid to flow therebetween in either direction.

The body 110 comprises reagent 111, which is a means for determining a characteristic of fluid disposed in the body. The reagent comprises a pH indicator which will change colour upon contact with a fluid, the final colour being dependent upon the acidity of the fluid. The apparatus 100 therefore allows the acidity of a fluid that is pumped either way through a fluid carrying system to be determined.

The body 110 comprises a transparent window 112 through which the reagent 111 is visible. This serves as a visual indicator means.

In use, a first end of an internal feeding tube releasably engages with the first protrusion 121, the first reduced diameter section 122 being pushed into the internal feeding tube (not shown) to form a good seal. The second, distal end of said feeding tube is disposed inside a patient to be fed and may or may not be disposed in that patient's stomach. Said feeding tube may be any type of feeding tube and in particular may be a nasogastric feeding tube or a percutaneous endoscopic gastrostomy (PEG).

A second feeding tube engages with the second protrusion 131, the second reduced diameter section 132 being pushed into the second feeding tube (not shown) to form a good seal. The second feeding tube connects the apparatus 100 to a bi-directional infusion pump (not shown) which is operable: to pump internal fluid from a reservoir, through the apparatus and into the internal feeding tube; and to pump fluid from the patient into the body 110 of the apparatus 100.

Therefore, in use, the apparatus 100 is connected in line between a feeding tube and a pump operable to pump internal fluid therethrough. Advantageously, this allows a user to ensure correct placement of internal feeding tubes prior to administering internal fluids. The pump is operated to pump fluid from the patient into the body 110 of the apparatus 100. Once in the body 110 the fluid will react with the reagent 111 which will change colour to a final colour indicative of the acidity of the fluid. If the acidity of the fluid matches that of gastric juices then it is assumed that the second, distal end of the feeding tube is disposed in the stomach of the patient and fluid can be safely administered via the feeding tube.

The principle is similar to a prior art technique but use of the apparatus according to the present invention reduces the number of connections and/or disconnections that need to be made to a feeding tube in order to aspirate a quantity of fluid therefrom and to introduce a quantity of fluid therein. Advantageously, this reduces the risk of contaminating the tube. This in turn can reduce the risk of infecting a patient that is being fed using the apparatus according to the present invention. The apparatus according to the present invention therefore simplifies the process; it can ensure that all necessary steps to check the location of a feeding tube are performed prior to feeding; it reduces the number of physical operations required of the user; and it reduces the risk that a user will come into contact with bodily fluids of a patient. The apparatus according to the present invention also reduces the amount of medical waste that must be disposed of relative to prior art techniques.

A non-return valve (not shown) is provided and is disposed between the apparatus 100 and the pump. Advantageously, this allows the pump to aspirate fluid out of the feeding tube and into the apparatus 100 so that its acidity may be determined whilst preventing the aspirated fluid from entering the pump.

The apparatus 100 may comprise a comparison means (not shown). The comparison means 100 may be operable to compare the acidity of the fluid drawn out of the enteral feeding tube as determined by the reagent 111 with predetermined criteria. For example, the criteria may require that the pH value of the fluid lies in a certain range. Preferably, this range coincides with the typical range of pH values of gastric juices. The comparison means may be operable to output a signal indicating whether or not the predetermined criteria are met. Said signal may be a digital signal.

The apparatus 100 may comprise a means for adjusting the flow of fluid through the body such as a valve (not shown). This can allow the speed and pressure to be varied for different feeding tube gauges.

Preferably, the apparatus 100 is provided as a single closed system. The single closed system is produced in sterile conditions and packaged so as to remain sterile until a user opens the packaging. Such an arrangement need only be removed from its sterile packaging and engaged with an internal feeding tube and a second feeding tube. Advantageously, this minimises the number of operations that must be performed by the user in a non-sterile atmosphere which in turn reduces the risk of contaminating the first fluid carrying element and limits the risk of infecting a patient.

Figure 4:
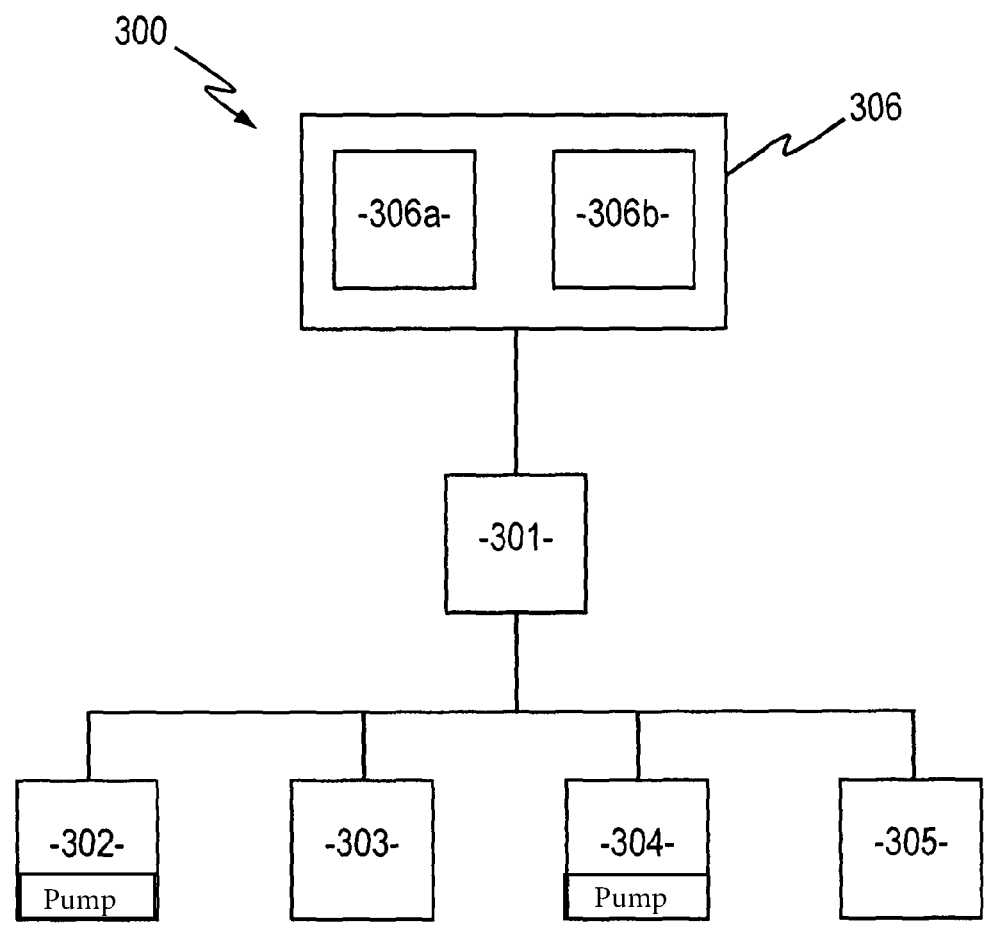
FIG. 4 is a schematic diagram of the control system for an embodiment of an apparatus according to the second aspect of the present invention.

Referring now to FIG. 4, an embodiment of a control system 300 for an apparatus according to the second aspect of the present invention is shown.

The apparatus comprises: an engagement means (not shown) arranged to allow releasable engagement of the apparatus with a first end of a tube (not shown); a means 302 for drawing fluid out of the first end of the tube; a means 303 for determining a characteristic of fluid drawn out of said tube; and a means 304 for introducing fluid into the first end of the tube. The apparatus further comprises a comparison means 305. The comparison means 305 is operable to compare the characteristic of the fluid drawn out of the tube as determined by the means 304 with predetermined criteria.

The apparatus comprises a processing means 301 which may be programmable. The processing means is connected to and able to control: the means 302 for drawing fluid out of the first end of the tube; the means 303 for determining a characteristic of fluid drawn out of said tube; the means 304 for introducing fluid into the first end of the tube; and the comparison means 305.

The apparatus is provided with a control unit 306 which is also connected to the processing means 301. The control unit comprises a input means 306a and a display means 306b. The control unit 306 provides a user interface for the processing means 301. The input means 306a may comprise one or more buttons, a touchpad or any other means for inputting control commands. The display means 306b may comprise a transparent section of the housing, an LCD display, an LED display or any other visual indication as desired or required.

The above embodiments are described by way of example only. Many variations are possible without departing from the scope of the invention as defined in the appended claims.

The invention claimed is:

1. An apparatus suitable for use in a tube feeding system, said apparatus comprising a body provided with a first opening and a second opening, wherein: a first engagement section is provided to allow releasable engagement of the apparatus with a first fluid carrying element so that the first opening is aligned with said first fluid carrying element; a second engagement section is provided to allow releasable engagement of the apparatus with a second fluid carrying element so that the second opening is aligned with said second fluid carrying element; and the first and second openings are connected so as to allow fluid to flow therebetween in either direction, wherein the body comprises a characteristic indicator, wherein the characteristic indicator determines a characteristic of fluid disposed therein; and
  wherein the second fluid carrying element is connected to a pump, and wherein the pump draws fluid out of the first fluid carrying element and into the body; and wherein the pump introduces fluid into the first fluid carrying element via the body and the second fluid carrying element.

2. The apparatus as claimed in claim 1 wherein the characteristic indicator comprises a reagent.

3. The apparatus as claimed in claim 1 wherein the pump is provided with a non-return valve.

4. The apparatus as claimed in claim 1 wherein the apparatus comprises a control system operable to compare the characteristic of the fluid drawn out of the first fluid carrying element with predetermined criteria and output a signal indicating whether or not the predetermined criteria are met.

5. The apparatus as claimed in claim 4 wherein if the predetermined criteria are not met, the pump is disabled or locked so as to prevent fluid from being introduced into the first fluid carrying element.

6. The apparatus as claimed in claim 1 wherein the apparatus comprises a visual indicator operable to display a visual indication of the characteristic of the fluid drawn out of the first fluid carrying element.

7. The apparatus as claimed in claim 1 wherein the apparatus comprises a flow valve, the flow valve adjusting the flow of fluid through the body.

8. A method of determining a location of a first end of a feeding tube using the apparatus of claim 1, wherein the first fluid carrying element is the feeding tube, the method comprising the steps of: releasably engaging the apparatus with a second end of the feeding tube using the first engagement section; releasably engaging the apparatus with the pump wherein the pump draws fluid out of and introduces fluid into the feeding tube and into the apparatus via the second fluid carrying element, using the second engagement section; using said pump to draw a quantity of fluid out of the feeding tube and into the apparatus; and determining the characteristic of said fluid drawn into the apparatus.

9. A feeding system comprising:
  a first fluid carrying element;
  a second fluid carrying element proximal the first fluid carrying element;
  an apparatus comprising a body provided with a first engagement section defining a first opening and a second engagement section defining a second opening, wherein the first engagement section is releasably engaged with the first fluid carrying element so that the first opening is aligned with the first fluid carrying element, and wherein the second engagement section is releasably engaged with the second fluid carrying element so that the second opening is aligned with the second fluid carrying element, the first and second openings are connected so as to allow fluid to flow therebetween in either direction, and wherein the body comprises a characteristic indicator, wherein the characteristic indicator determines a characteristic of the fluid disposed therein; and a pump being connected to the second fluid carrying element such that the pump is operable to draw fluid out of the first fluid carrying element and into the body and the pump is operable to introduce fluid into the first fluid carrying element via the body and the second fluid carrying element.

\* \* \* \* \*